United States Patent [19]

Pacey et al.

[11] Patent Number: 5,683,570
[45] Date of Patent: Nov. 4, 1997

[54] GAS DETECTION METHOD

[75] Inventors: Philip D. Pacey, Halifax; Hiroshi Furue, Dartmouth, both of Canada

[73] Assignee: Dalhousie University, Halifax, Canada

[21] Appl. No.: 417,464

[22] Filed: Apr. 5, 1995

Related U.S. Application Data

[63] Continuation of Ser. No. 72,464, Jun. 4, 1993, abandoned.

[51] Int. Cl.⁶ .................................................. G01N 27/409
[52] U.S. Cl. ........................... 205/784; 204/424; 204/427; 205/783.5; 205/787
[58] Field of Search ............... 204/153, 18, 421–429; 205/787, 783.5, 784, 784.5, 785

[56] References Cited

U.S. PATENT DOCUMENTS

| | | |
|---|---|---|
| 3,216,911 | 11/1965 | Kronenberg . |
| 3,347,767 | 10/1967 | Hickam . |
| 3,464,008 | 8/1969 | Meysson et al. ............. 204/422 |
| 3,514,377 | 5/1970 | Spacil et al. . |
| 3,598,711 | 8/1971 | Flais ............................. 204/427 |
| 3,616,408 | 10/1971 | Hickam . |
| 3,620,931 | 11/1971 | Reichner ..................... 204/426 |
| 3,773,641 | 11/1973 | Fitterer ......................... 204/423 |
| 3,791,936 | 2/1974 | Pebler et al. ................. 204/427 |
| 3,843,400 | 10/1974 | Radford et al. .............. 204/421 |
| 3,860,498 | 1/1975 | Jones . |
| 3,923,624 | 12/1975 | Beekmans et al. . |
| 4,005,001 | 1/1977 | Pebler ........................... 204/426 |
| 4,134,818 | 1/1979 | Pebler et al. ................. 204/427 |
| 4,327,122 | 4/1982 | Chakupurakal .............. 204/427 |
| 4,370,393 | 1/1983 | Watanabe et al. ........... 204/421 |
| 4,388,411 | 6/1983 | Lovelock . |
| 4,663,017 | 5/1987 | Ross . |
| 4,749,466 | 6/1988 | Masson et al. . |
| 4,980,044 | 12/1990 | Ker . |

FOREIGN PATENT DOCUMENTS

| | | |
|---|---|---|
| 816281 | 6/1969 | Canada . |
| 823776 | 9/1969 | Canada . |
| 973931 | 9/1975 | Canada . |
| 1004731 | 2/1977 | Canada . |
| 1015827 | 8/1977 | Canada . |

(List continued on next page.)

OTHER PUBLICATIONS

E. Hafele, K. Kaltenmaier and U. Schonauer; Application of the $ZrO_2$ Sensor Determination of Pollutant Gases; 1991.

*Primary Examiner*—T. Tung
*Attorney, Agent, or Firm*—Robert W. Becker & Associates

[57] ABSTRACT

A method is provided for measuring the concentration of a sample gas in an oxygen-containing carrier gas by continuously flowing the oxygen-containing carrier gas which also contains the sample gas whose concentration is to be measured, into and through a central, solid electrolyte inner detector tube, having a particular configuration to eliminate back-diffusion of air thereinto, the inner detector tube having an internal electrode, provided with a first, electrically-conductive output lead, in contact with its interior surface, and an external electrode, provided with a second, electrically-conductive output lead, in contact with its external surface. This bathes a first interface comprising the internal electrode and the interior of the inner detector tube with only the continuously flowing oxygen-containing carrier gas, at a predetermined temperature. A reference gas is also continuously flowed into the annulus between the inner detector tube and an outer, concentric non-porous tube, having a particular configuration to eliminate back-diffusion of air into such annulus. This bathes a second interface comprising the external electrode and the exterior of the inner detector tube with only the continuously flowing reference gas, at that temperature. The carrier gas and the reference gas are prevented from intermingling by a particular structural relationship. An electrical signal is generated between the electrodes, the electrical signal being directly proportional to the concentration of the sample gas to be determined. The so-generated electrical signal is measured to determine the concentration of the sample gas as a linear correlation of the electrical signal.

19 Claims, 4 Drawing Sheets

FOREIGN PATENT DOCUMENTS

| | | |
|---|---|---|
| 1054224 | 5/1979 | Canada . |
| 1058706 | 7/1979 | Canada . |
| 1060097 | 8/1979 | Canada . |
| 1128610 | 7/1982 | Canada . |
| 1164946 | 4/1984 | Canada . |
| 1167527 | 5/1984 | Canada . |
| 1170720 | 7/1984 | Canada . |
| 1221415 | 5/1987 | Canada . |
| 2001883 | 10/1989 | Canada . |
| 2002482 | 11/1989 | Canada . |

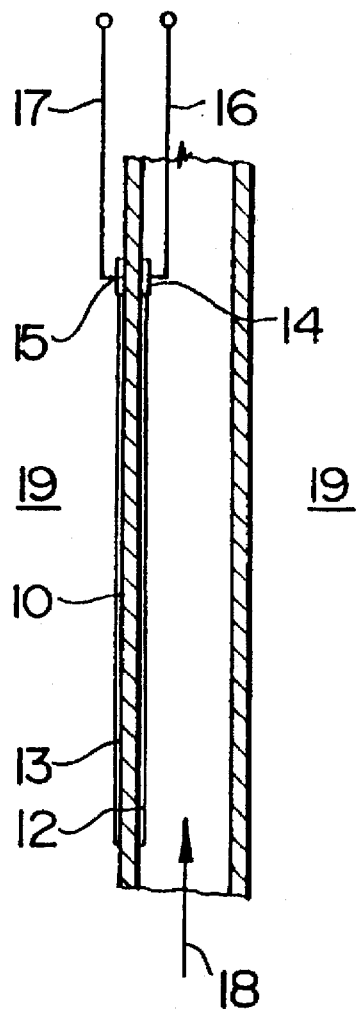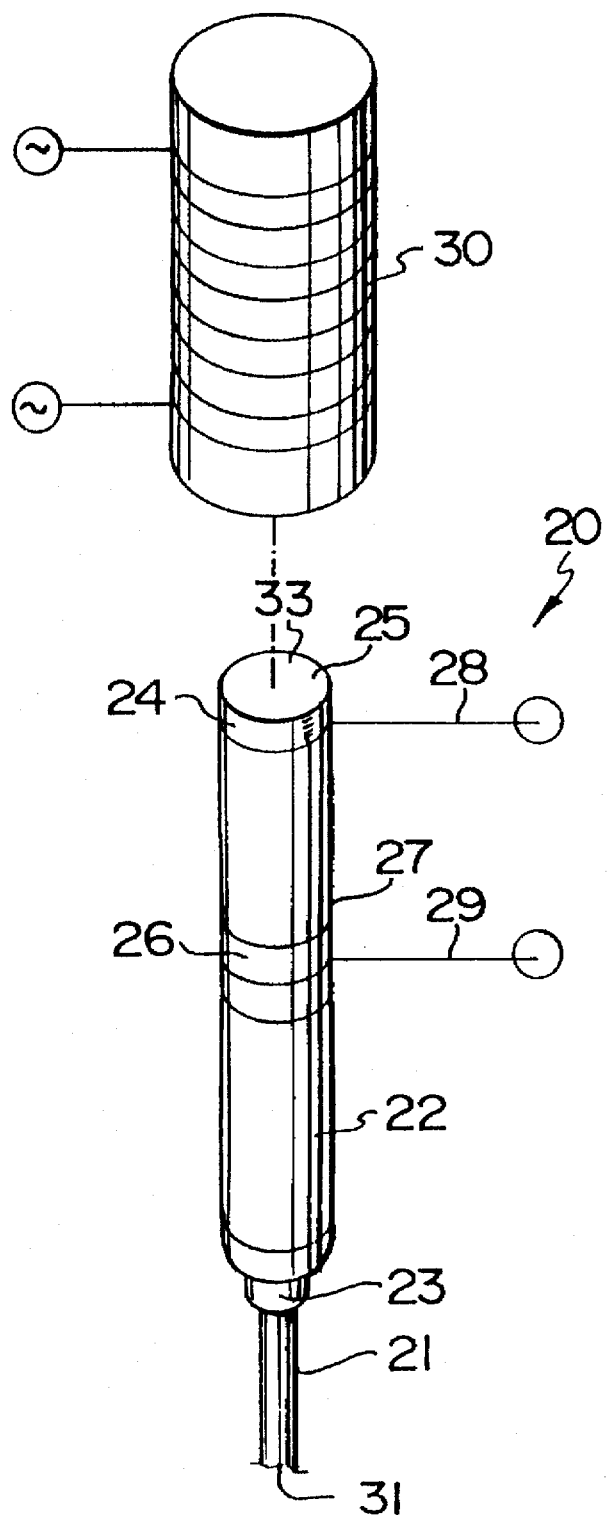
FIG.1
FIG.2

GAS DETECTION METHOD

This application is a continuation of application Ser. No. 08/072,464 filed Jun. 4, 1993, now abandoned.

BACKGROUND OF THE INVENTION (i) Field of the Invention

This invention relates to gas detection and analysis.

(ii) Description of the Prior Art

There is substantial need to be able to analyze gases routinely, simply, and rapidly. In industrial situations, and also in hospitals and educational institutions, gases are used. Leaks may occur which could be injurious to health. It is essential to have rapid means of detecting such leaks before they can cause injuries or fatalities. Frequently such gases have a dulling effect on response on the part of humans and, thus, individuals are incapable of dealing with an emergency leak unless the leak is detected at extremely low levels. In such cases it is also frequently important to be able to identify the gas.

A second major area of use is for analysis of gases. In industrial circumstances it is desirable to be able to know what are the constituents and their quantities in a gas stream in order to optimize performance. It is also desirable to be able to analyze gases in research.

Oxygen sensors based on the principle of solid electrolyte galvanic cells essentially contain an oxide-ion conductive ceramic body with electrodes in contact with opposite faces of the body. One electrode is exposed to a reference source of oxygen. The other electrode is exposed to a source whose oxygen content is to be determined. When the pressure or partial pressure of oxygen at the two electrodes is different, a potential is developed between them, which is the sensor output voltage.

Such sensors have wide commercial and industrial application. Non-limiting examples include the following:

1. Solid electrolyte ceramic sensors are used widely to monitor the oxygen content of the exhaust gas produced by an internal combustion engine. The sensor output voltage is used to regulate the efficiency of the engine by providing feedback to a device that controls the air-to-fuel ratio. In one type of such sensor, the solid electrolyte has the general shape of a thimble and comprises a stabilized zirconia material, with platinum electrodes formed on the interior and exterior surfaces of the material. Typically, such a sensor operates at exhaust temperatures above about 400° C. and requires some time to heat up before it becomes responsive. An auxiliary electrical heater may be incorporated in the sensor to overcome this limitation.

2. Solid electrolyte sensors may be used for the quantitative measurement of oxygen pressure inside a vacuum chamber over the range 1 to $10^{-7}$ Torr.

3. Electrochemical oxygen sensors are also used for the determination of the concentration of oxygen in molten metals.

4. Other major applications of solid electrolyte sensors are in the glass and ceramic industries as, for example, in monitoring the oxygen content of molten glass or in monitoring the partial pressure of oxygen in ceramic kilns to control the colour of glazes. They are also used in direct reduction kilns for the production of iron, in copper smelting reverbatory furnaces, and in furnaces for the heat-treatment of metals as, for example, in gas carburizing for the hardening of metal surfaces. They are also used extensively to measure the oxygen content of boiler flue gases. They may be employed as safety devices in which the sensor output voltage is connected to an alarm system to warn of impending explosive mixtures if a combustion process fails.

By constant monitoring and controlling the atmosphere in such processes, considerable savings in fuel can be effected. The location of the probe is often an important consideration. In some applications, for example, it may be desirable to locate the sensor close to a flame, to indicate the partial pressure of oxygen in the combustion gases at that point. In other applications it may be desirable to locate the sensor at a position remote from the source of combustion as, for example, in a flue or stack, to indicate the average partial pressure of oxygen in the products of combustion. The probes should thus be capable of responding accurately over a wide range of temperatures and/or oxygen pressures. Such probes may also have to retain their operating characteristics over periods of months or even years of service and it is important in such cases that the probe should not be susceptible to what is commonly termed aging, i.e. changes in the sensor output voltage over prolonged usage. The time of response of the probe to rapid changes in pressure or partial pressure of oxygen is important in many applications. The passage of oxygen through the probe should be minimal, so that the sensor output voltage corresponds closely to the true value of the oxygen pressure or concentration to be determined.

In the field of gas analysis, there are several devices which may serve as a specific warning for the presence of particular gases, usually based on some specific reaction or absorption which occurs. For quantitative analysis, there are gas chromatographic, mass spectrometric, and various spectroscopic techniques.

The existing devices have limitations. The molecule-specific detection schemes only detect one gas and it would be necessary to have a large array of these in order to detect the variety of gases which could be present in a system. One detector would be needed for each potential type of gas molecule. A mass spectrometer is not a robust device. It requires careful attention to high vacuum techniques. It can be easily contaminated by a variety of gases. It produces patterns of peaks which are characteristic for a particular molecule, but when a mixture of molecules is present it is very difficult to tell which peaks come from which molecules. A high quality mass spectrometer is extremely expensive. The spectroscopic techniques are typically only applicable to a single gas at a single time. One wavelength of light may interact with one particular molecule but there may be interferences from another type of molecule. Sensitivities are generally low because of the small density of molecules present in the gas phase. There can be overlapping peaks which inhibit identification.

The patent literature also provided gas detection/measurement devices. Canadian Patent No. 1,015,827 patented Aug. 16, 1977 by J. W. Riddel provided a zirconia oxygen concentration cell for use as an air/fuel ratio sensor for an automotive internal combustion engine. The patented air/fuel ratio sensor for an automotive exhaust system was one in which the zirconia body had two opposed faces exposed to the exhaust gases and none to a separate reference gas. There was a catalytic electrode on one face, but there was a non-catalytic electrode on the other face. The body was mounted in an exhaust pipe with both electrodes exposed to the exhaust gases.

Canadian Patent No. 1,170,720 patented Jul. 10, 1984 by D. F. Ross et al provided a modified zirconia oxygen sensor wherein gas flowed through inner and outer tubes. One electrode was on the inner surface of the inner tube and the second electrode was on the outer surface of the inner tube. The outer catalytic surface was made inert by means of a cement or other material which poisoned its catalytic activity. Because of the tubular configuration, sample gas flow was split, so that gas flow existed on both sides of the inner tube, and there was no mixing of the reacted and unreacted gas.

U.S. Pat. No. 4,749,466 patented Jun. 7, 1988 by C. R. Masson et al provided a solid electrolyte oxygen sensor in which the solid electrolyte was a solid electrolyte ceramic body comprising an oxide of a tetravalent element selected from the group consisting of zirconia, thoria and hafnia, doped with an oxide of an element of less valence than four selected from the group consisting of yttria, lime and magnesia, wherein the weight percentage of impurities of all oxides of variable valence elements combined is no greater than 0.02, while the weight percentage of all oxides of fixed valence elements combined is at least 0.5%.

SUMMARY OF THE INVENTION

(i) Aims of the Invention

However, none of the prior art devices solve the problem of providing an inexpensive gas detection device which is also of very high sensitivity.

Accordingly it is an object of this invention to provide gas detection which is inexpensive.

Another object of this invention is to provide gas detection of high sensitivity.

Another object of this invention is to provide a gas sensor which is sensitive to molecules for which a flame ionization detector is not usually sensitive.

Another object of this invention is to provide a gas sensor which gives a linear electrical signal response.

(ii) Statement of Invention

By this invention, a system is provided for gas detection, and/or identification and/or analysis comprising: a) a central tube, having means for the inlet of a gaseous mixture containing the gas to be detected, and/or identified and/or analyzed and gas outlet means, the central tube being formed of a solid electrolyte comprising an oxide of a tetravalent element, e.g., zirconia, thoria, or hafnia, preferably zirconia, doped with an oxide of an element of less value than four, e.g., yttria, lime or magnesia, preferably yttria; b) an inner electrode band around the inner surface of the central tube, the inner electrode band being electrically connected to a first electrically-conductive output lead; c) an outer electrode on the outer surface of the central tube, the outer electrode band being electrically connected to a second electrically-conductive output lead; d) an annular tubular member, concentrically disposed around the central tube, the tubular member having means for the inlet of a carrier gas, and gas outlet means, the annular tubular member being formed of a non-conductive, non-porous material; e) a heater surrounding the annular tubular member at the region of the electrode bands to maintain the electrode-solid electrolyte interface at a selected temperature; and f) means for measuring either voltage or current values from the output leads to enable detection of the gas, and/or identification of the gas, and/or analysis of the gas.

By this invention, a method is also provided for measuring the concentration of a sample gas in an oxygen-containing carrier gas comprising the steps of: (a) continuously flowing the oxygen-containing carrier gas which also contains the sample gas whose concentration is to be measured, by way of entry through a first inlet tube into and through a central, solid electrolyte inner detector tube, the first inlet tube being disposed at one end of the central, solid electrolyte inner detector tube, and by way of discharge through a first outlet tube therefrom at the other end thereof, the first outlet tube substantially eliminating back-diffusion of air into the central, solid electrolyte inner detector tube, the central, solid electrolyte inner detector tube comprising an oxide of a tetravalent metal doped with an oxide of an element having a valence less than four, the central solid electrolyte inner detector tube being provided with an internal electrode in contact with the interior of the central, solid electrolyte inner detector tube, the internal electrode being provided with a first, electrically-conductive output lead, and also with an external electrode which is in contact with the exterior of the central, solid electrolyte inner detector tube, the external electrode being provided with a second, electrically-conductive output lead, whereby to bathe a first interface comprising the internal electrode and the interior of the central, solid electrolyte inner detector tube only with the continuously flowing oxygen-containing carrier gas which also contains the sample gas, the interface being maintained at a predetermined temperature; (b) continuously flowing a reference gas by way of entry through a second inlet tube into and through an annulus between the central, solid electrolyte inner detector tube and an outer, concentric non-porous tube, the second inlet tube being disposed at one end of the annulus between the central, solid electrolyte inner detector tube and same outer concentric, non-porous tube, and by way of discharge through a second outlet tube from the annulus between the central, solid electrolyte inner detector tube and the outer, concentric non-porous tube at the other end thereof, the second outlet tube substantially eliminating back-diffusion of air into the annulus, whereby to bathe a second interface comprising the external electrode and the exterior of the central, solid electrolyte inner detector tube only with the continuously flowing reference gas, the interface being maintained at the same predetermined temperature as recited hereinabove in step (a); (c) sealing the first inlet tube to, the first outlet tube from, the second inlet tube to, and the second outlet tube from the central, solid electrolyte inner detector tube and the outer concentric non-porous tube to provide a sealed unit; (d) both the oxygen-containing carrier gas which also contains the sample gas, and the reference gas having a low level, impurity concentration of oxygen; (e) generating an electric signal between the electrodes, the electrical signal being directly proportional to the concentration of the sample gas to be determined; and (f) measuring the electrical signal to determine the concentration of the sample gas as a linear correlation of the electrical signal.

(iii) Other Features of the Invention

By a feature of the system of this invention, the central tube is composed of 92 mol % zirconia/8 mol % yttria. By another feature of the system of this invention, the inner electrode band is formed of platinum. By yet another feature of the system of this invention, the outer electrode comprises at least one strip of platinum along the longitudinal axis of the tube. By an embodiment of this feature of the system of this invention, the outer electrode comprises an encircling band of platinum. By a further feature thereof, the annular tubular member is formed of quartz.

By one especial embodiment of the system of this invention, the central tube is composed of 92 mol % zirconia/8 mol % yttria; the inner electrode band is formed of platinum; the outer electrode comprises at least one strip of platinum along the longitudinal axis of the tube; and the annular tubular member is formed of quartz.

By another especial embodiment of the system of this invention, the central tube is composed of 92 mol % zirconia/8 mol % yttria; the inner electrode is an encircling band formed of platinum; the outer electrode comprises at least one strip of platinum along the longitudinal axis of the tube; and the annular tubular member is formed of quartz.

By yet another feature of the system of this invention, the inner electrode comprises a platinum band at the mid-region of the tube, and the outer electrode comprises a platinum band at the mid-region of the tube.

By still another feature of the system of this invention, the system includes a temperature monitor within or near the tube to monitor temperature, e.g., within the range of about 540°–695° C.

By a further feature of the system of this invention, the gas outlet is a top opening of the tube. By an embodiment of such feature of the system of this invention, the system is enclosed by a gas-impervious dome, whereby carrier gas effluent envelopes the outer electrode and escapes through an opening at the bottom. By still another embodiment of such feature of the system of this invention, two gas inlet means are provided, one inlet means being for conveying carrier gas in an annular zone between the inner and outer tubes, the other inlet being means for conveying a carrier gas/sample gas mixture within the inner tube.

By one feature of the method of this invention, a carrier gas containing an organic vapor is caused to come into contact with the first electrode in the first tube, and a gas containing a fixed percentage of oxygen is caused to come into contact with the second electrode in the second tube. In this embodiment of this feature of the method of this invention, the electrical signal may be a voltage, to indicate the content and nature of the organic vapors. Alternatively, in this embodiment of this feature of this invention, the electrical signal may be current, to indicate the nature and amount of the organic vapors.

By another feature of the method of this invention, the method includes the step of flowing a carrier gas containing non-uniform slugs or peaks of organic vapours through the inside of the first, i.e. inner, tube.

By yet another feature of the method of this invention, the organic vapor may react with oxygen pumped electrochemically through the solid electrolyte by placing a positive voltage on the electrode in contact with the organic vapor and placing a negative voltage in the electrode on the other side of the solid electrolyte in contact with a gas containing oxygen. In this feature of the method of this invention, different voltages may be applied to the solid electrolyte to provide for qualitative analysis of organic vapors, and to provide the amount of oxygen pumped through the solid electrolyte to react with the organic vapors and provide an analysis. In a still further embodiment of this method of this invention, the quantitative analysis may be determined by measuring steady state current passing through the solid electrolyte. In still another embodiment of this method of this invention, the quantitative analysis may be determined by measuring the total amount of charge passed through the solid electrolyte. In yet another embodiment of this method of this invention, a ramp may be applied to the voltage so that different groups of compounds react at different voltages, in order to generate a series of peaks as a function of time. In an especially preferred variation of this method of this invention, the method includes setting a plurality of electrodes at different voltages, or at different temperatures, to give optimum analyses of organic or inorganic compounds.

By a still further feature of method of this invention, the oxygen may be pumped out of organic molecules by placing a negative voltage on the electrode in contact with the organic vapor, and placing a positive voltage on the electrode on the other side of the solid electrolyte in contact with a flowing gas. In one embodiment of this method of this invention, different voltages are applied to the solid electrolyte to provide for qualitative analysis of organic vapors. In a still further embodiment of method of this invention, the quantitative analysis may be determined by measuring steady state current passing through the solid electrolyte. In a still further embodiment of this method of this invention, the quantitative analysis may be determined by measuring the total amount of charge passed through the solid electrolyte. In yet a further embodiment of the method of this invention, a ramp may be applied to the voltage so that different groups of compounds react different voltages, in order to observe a series of peaks as a function of time. In an especial variation of the method of this invention, the method includes setting a plurality of electrodes at different voltages, or at different temperatures, to give optimum analyses of organic or inorganic compounds.

(iv) Generalized Description of the Invention

Thus the present invention provides a specialized form of a solid electrolyte detector for gas chromatography. Zirconia, the preferred solid electrolyte, is a solid electrolyte at high temperatures. When heated and subjected to a pressure gradient of oxygen between two sides of a zirconia plate, electromotive force (emf) is produced according to the Nernst equation. This phenomenon is utilized here for the first time to detect trace amounts of combustible gases in gas chromatography. When a carrier gas flows through a tube made of zirconia and is heated, for example, at above about 500° C. the inside surface is exposed to the impurity concentration of oxygen in the carrier gas and the outside surface to the oxygen concentration in a second gas. When electrodes, e.g., of platinum, are placed on both surfaces, this oxygen pressure gradient produces a certain electric potential and induces a certain electric current if a circuit loop is formed. The values of voltage and current depend on the concentration of oxygen in the carrier gas and the second gas. If the carrier gas carries a small amount of combustible gases, as in the case of gas chromatography, the combustible gases oxidize at the inside electrode and consume some of the oxygen present in the carrier gas. This process increases the oxygen pressure gradient and thus causes the increase in the voltage output and the current flow.

As is clear from the above description, the basis of this invention is the use of a solid electrolyte, i.e., a zirconium oxide electrolyte with metal or metal oxide electrodes at points on the inside and outside of the tube. A gas containing an organic vapour is allowed to come into contact with the inside or the outside of this tube while the other surface is in contact with a gas containing a fixed percentage of oxygen. An electrical signal will be obtained from the tube which will indicate the content and nature of the organic vapours. This electrical signal may be a voltage signal. Alternatively, either a fixed or varying voltage signal may be applied to the electrodes, in which case the current carried between the electrodes will constitute the electrical signal giving information regarding the nature and amount of the organic vapours.

There are many embodiments of this invention. As is clear from the above, in its simplest form, the inventive device may comprise a tube or thimble made of zirconia with a metal paste, e.g., platinum, on the outside and on the inside and with electrodes connected to the paste. When gas containing oxygen is in contact with both the inside and the outside of the tube, a voltage is produced which is dependent on the ratio of oxygen concentrations on the inside and on the outside of the tube. The zirconia tube includes means for its heating. When an organic vapour is present in either gas, it reacts on the platinum or other metal or metal-oxide electrode with the oxygen in the gas, reducing the partial pressure of oxygen in equilibrium with the electrode and changing the detector voltage. This change in voltage then constitutes the signal.

This invention provides a new use of such a detector, i.e., to the effluent stream from a gas chromatograph. It is possible to control the oxygen content of the carrier gas to a low level. Under these circumstances the detector is extremely sensitive and may rival or exceed the sensitivity of known gas chromatograph detectors. The sensitivity is closely linked to the concentration of oxygen in the carrier gas. For such use it is more convenient to have the carrier gas, which contains peaks or slugs of organic vapour, pass through the inside of the zirconia tube. In such a case the sensitivity of the detector for various molecules would depend upon the amount of oxygen with which molecules would react on combustion. For example: at complete combustion, a carbon atom in a molecule would react with one molecule of $O_2$ to form carbon dioxide; a hydrogen atom would react with a quarter of a molecule of $O_2$ to form $H_2O$; and an oxygen atom in a molecule would displace half a molecule of $O_2$ so the relative response of molecules would be C+¼ H-1/20. This may be contrasted with the response of a flame ionization detector which is simply proportional to the carbon content of the molecules.

In another embodiment of the inventive device, the oxygen needed to react with the organic vapour is not present initially in a mixture with the vapour but instead is pumped electrochemically through the zirconia. This is achieved by placing a positive voltage on the electrode in contact with the organic vapour and placing a negative voltage on the electrode on the other side of the zirconia in contact with oxygen gas or air. The voltage draws oxygen through the zirconia as oxide anions. When such anions reach the surface of the zirconia, they react with the organic vapour. If carried to completion, the reaction again would involve one oxygen molecule reacting with each carbon, with a quarter of each hydrogen, one with every four hydrogen atoms, and with each oxygen atom in the organic molecule requiring half a molecule of oxygen less.

Alternatively, in another use according to this invention, only the first step is the oxidation of the organic vapour. The zirconia again would be heated. Different molecules would react with the oxygen being pumped through the zirconia at different applied voltages. This would provide a means of qualitative analysis of the organic vapours, that is, to distinguish between alcohols, ethers, aldehydes, ketones, acids, etc. The amount of oxygen pumped through the zirconia to react with these vapours would give a measure of the amount of organic vapour present. This would be measured by determining the current passing through the zirconia in a steady state situation or by determining the total amount of the charge passed through the zirconia in the case of a peak or a pulse of organic vapour coming in contact with the electrode of the zirconia.

Coulometric detectors have been used in the liquid phase and have been used for analysis of oxygen with zirconia sensors; these have not been used for analysis of organic vapours. Such coulometric detectors, involving the use according to the process of this invention, would be used to analyze the effluent from a gas chromatograph column. In order to determine quantities different classes of compounds present, a ramp would be applied to the voltage so that different groups of compounds would react at different voltages. A series of peaks would be observed as a function of time. Several electrodes could be placed on a zirconia tube, e.g., by being painted in bands around the tube. These are then set at different voltages or at different temperatures so as to give the optimum analysis for the different classes of compounds. Such a device would not be limited to organic compounds, but is also useful to analyze some inorganic compounds, e.g., carbon monoxide, hydrogen and HCN, which are capable of reacting with oxygen at the surface of the detector.

A third use according to the present invention operates in reverse to the second one described above. The zirconia acts as a pump to suck oxygen, in effect, out of organic molecules. For this use, the reverse polarity would be applied. The negative electrode is in contact with the organic vapour and the positive electrode is in contact with the opposite side of the zirconia. Under these circumstances, oxygen anions would move from the negative to the positive electrode. They would be created at the positive electrode by reaction of the organic molecules which contain oxygen. These molecules would release their oxygen which would then be carried through the zirconia. The amount of charge carried would be a direct measure of the number of oxygen atoms present in the organic vapour. The oxygen is released by different classes of organic molecules, e.g., alcohols, ethers, aldehydes, ketones and acids, at different voltages and/or temperatures. The amount of current carried is measured in a steady state device. Where pulses of organic vapours come in contact with the zirconia, then the total amount of charge carried could be measured. In either case, the signal would be proportional to the amount of oxygen present.

The device of this invention is also useful to analyze the effluent from a gas chromatograph. Several classes of compounds could be separately analyzed by ramping the voltage and/or temperature or by using separate bands of electrode on the zirconia tube at different voltages and/or temperatures. A device at a low voltage is used to remove oxygen from the gas before analyzing the organic molecules for their oxygen content.

Another use according to this invention is achieved by combining the third detector with either the first or the second and a flame ionization detector. Then the FID would give "C"; the first or second detector would give "C"+ ¼"H"-½"O"; and the third detector would give "O". This would give three different equations for the elemental content "C", "H" and "O". This set of equations is solved electrically to give the "C", "H" and "O" content of a compound. In the prior art, such content is something which usually requires expensive and old-fashioned technology and the sending of the samples by mail. The method gives such an analysis rapidly for each peak in a gas chromatographic effluent, greatly aiding in the identification of peaks. It gives both the total amount of each compound present and its elemental analysis. In the event that compounds contained extra elements, then an extra detector, e.g., an electron capture detector, could be added to the system.

BRIEF DESCRIPTION OF THE DRAWINGS

In the accompanying drawings,

FIG. 1 is a schematic representation showing the principle of operation of the detector of the present invention;

FIG. 2 is a schematic perspective view, partially exploded, of one embodiment of the detector of the present invention;

Figure 3:
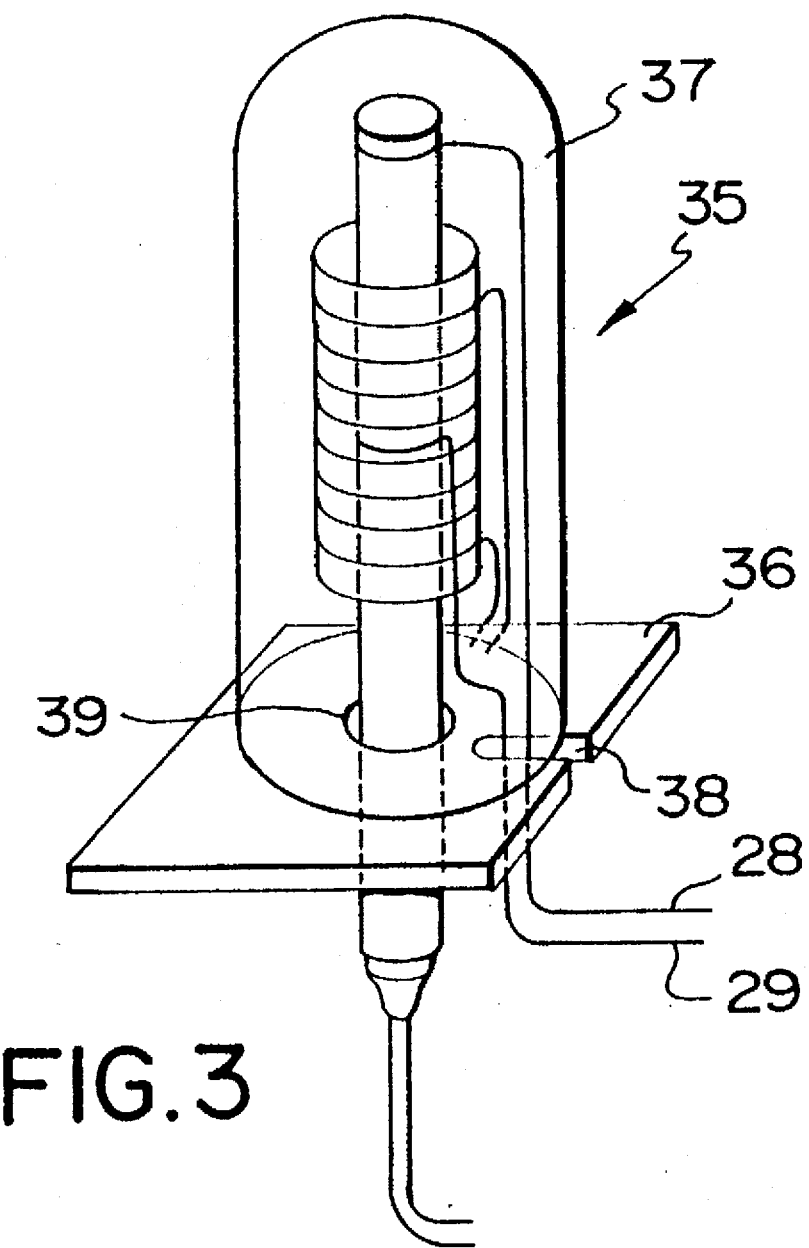
FIG. 3 is a schematic perspective view of another embodiment of the detector of the present invention.

DESCRIPTION OF PREFERRED EMBODIMENTS (i) Description of FIG. 1

As seen schematically in FIG. 1, a tube 10 is provided. The tube 10 is made of a suitable oxide-doped solid electrolyte, e.g., a yttria-doped zirconia, preferably containing 8 mol % $Y_2O_3$ and 92 mol % $ZrO_2$. On the inside wall of the tube 10 is a longitudinal electrode 12 formed of a platinum paste. On the outside wall of tube 10 is a longitudinal electrode 13 formed of a platinum paste. Inner 14 and outer 15 platinum connectors are interconnected between electrodes 12,13 and electrical leads 16,17. Gas 18 to be analyzed is fed as a feed to the interior of tube 10, while reference gas 19 bathes the outside of tube 10.

(ii) Description of FIG. 2

FIG. 2 shows a detector 20 comprising an inlet tube 21 and an outer concentric zirconia tube 22, with a silicone seal 23 therebetween. An outer band of platinum 24 is secured to the upper end 25 of outer open tube 22. An outer band platinum electrode 26 is secured to the mid-area 27 of outer open tube 22. The upper band 24 of platinum is electrically connected by a strip of platinum paint (not shown) to a second platinum paste electrode (not shown) which is on the inner surface of zirconia tube 22, opposite to the outer platinum electrode 26. An electrical lead 28 is connected to outer band 24 and a second electrical lead 29 is connected to outer platinum electrode 26. The electrical energy at leads 28,29 is the output of the detector 20.

An electric heater 30 is disposed concentrically around tube 22 to heat the electrode 26 to a suitable predetermined temperature for the detection of the gas in the gaseous flow of carrier gas and sample gas.

The carrier gas and sample gas are admitted to the inlet 31 of inlet tube 21 and escape through open ended outlet 33. A blanket bathing gas containing oxygen is admitted to the annular zone between tube 22 and heater 30, and escapes at the top of the detector.

(iii) Description of FIG. 3

FIG. 3 shows a detector 35 which includes all the elements of the detector 20 of FIG. 2 and so includes some of the same reference numbers. In addition, however, the detector 35 includes a base 36 and a dome 37 enveloping the detector 20 and supported on the base 36. Base 36 includes a slot 38 for the disposing of leads 28,29 and a lower annular aperture 39 for the escape of gases.

Figure 4:
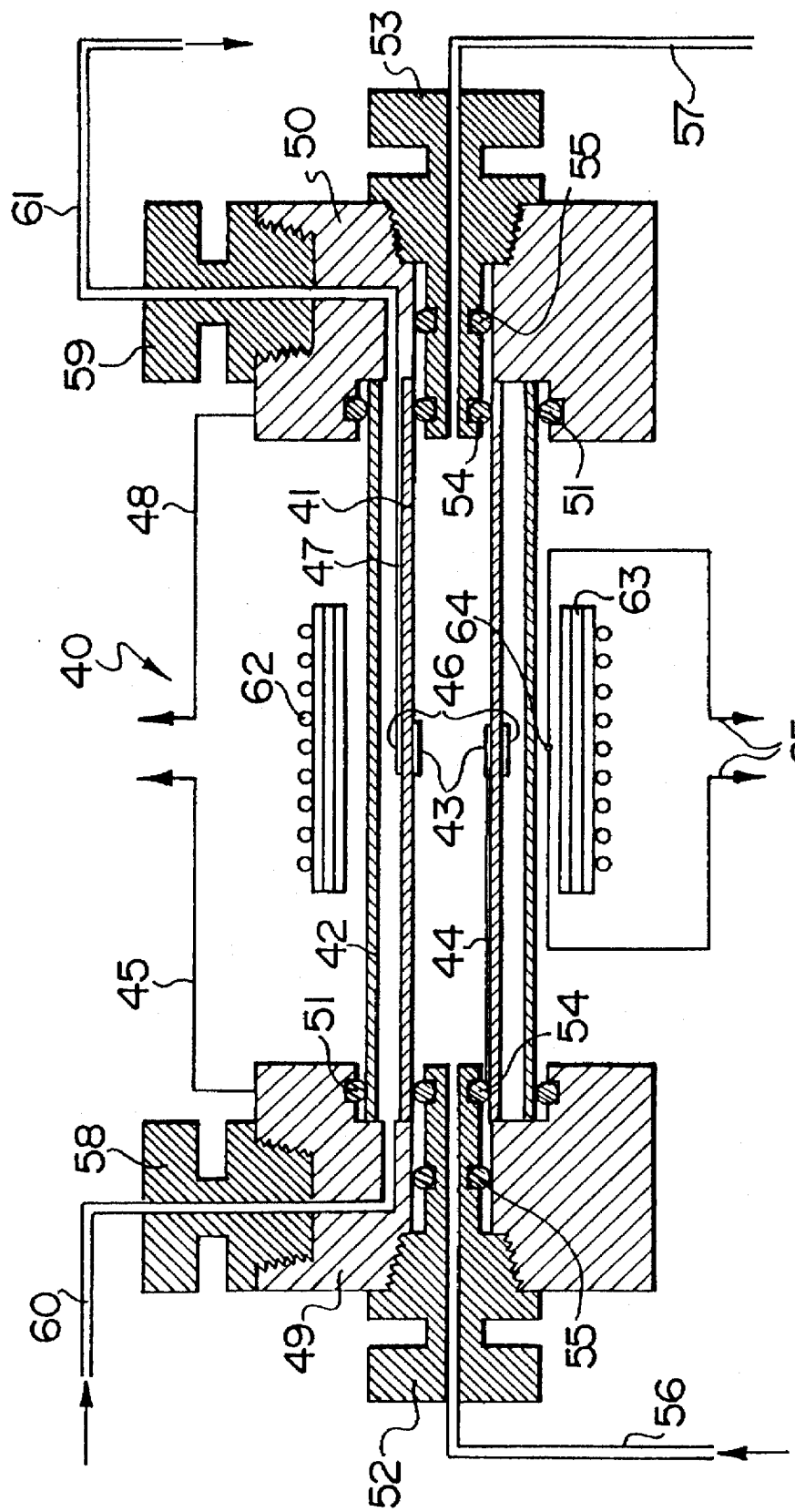
FIG. 4 is a central longitudinal section through yet another embodiment of the detector of the present invention.

(iv) Description of FIG.4

The detector 40 shown in FIG. 4 includes an inner detector tube 41 and an outer tube 42. Inner detector tube 41 is formed of, e.g., a yttria-doped zirconia containing 92 mol % zirconia and 8 mol % yttria, while outer tube 42 is formed of quartz. Tube 41 is provided with an inner band platinum electrode 43 joined by conducting platinum longitudinal strip 44 to electrical lead 45 via brass end piece 49. Tube 41 is also provided with external band platinum electrode 46 joined by conducting platinum longitudinal strip 47 to electrical lead 48 via brass end piece 50.

Tubes 41 and 42 are sealed as a unit by means of two brass end pieces 49,50 with two O-ring seals 51 between the brass end pieces 49,50 and outer tube 42. A brass inlet piece 52 and a brass outlet piece 53 are fitted to the brass end pieces 49,50 respectively for introduction to, and discharge from, the inner tube 41. Two O-ring seals 54 are disposed between inner tube 41 and inlet 52 and outlet 53 pieces and two O-ring seals 55 are disposed between end pieces 49,50 and outlet 52 and inlet 53 pieces.

Inlet piece 52 is fitted with copper inlet tube 56 leading to the core of inner tube 41 while outlet piece 53 is fitted with copper outlet tube 57 leading from the core of inner tube 41. Brass end pieces 49,50 are provided with inlet plug 58 and outlet plug 59 respectively. Inlet plug 58 is fitted with copper inlet tube 60 leading to the annulus between inner tube 41 and outer tube 42, while outlet plug 59 is fitted with copper outlet tube 61 leading from the annulus between inner tube 41 and outer tube 42.

A helical-wound heater 62 with a stainless steel noise shield 63 is disposed around the outer tube 42. A thermocouple 64 is disposed between the outer tube 42 and the heater 62 to provide temperature monitor lead lines 65.

Figure 5:
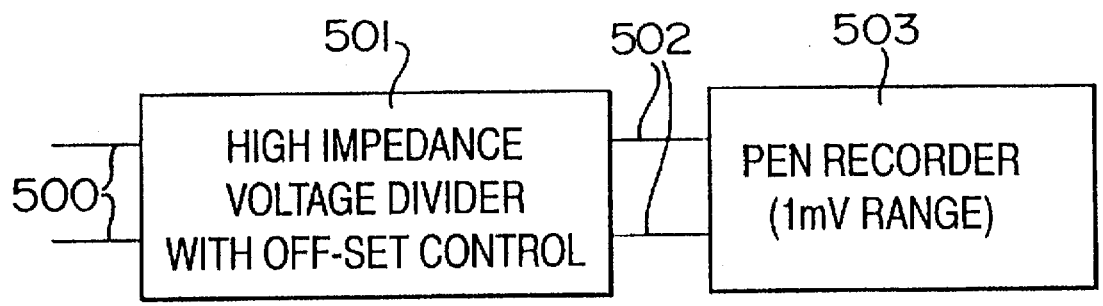
FIG. 5 is a schematic diagram of the electrical connection for voltage measurement of the detector of the present invention.

(v) Description of FIG. 5

As seen in FIG. 5, for voltage measurement, the output 500 from the detector is fed directly to a high impedance voltage divider with off-set control shown in block 501. The output 502 from block 501 is fed to a pen recorder 502 having a 1 mV range.

Figure 6:
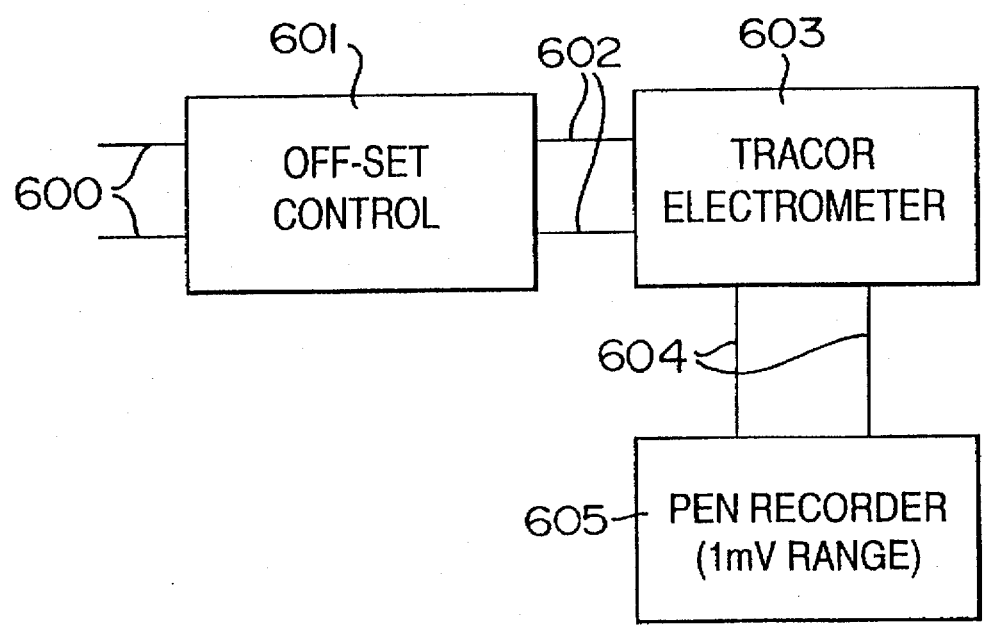
FIG. 6 is a schematic diagram of the electrical connection for current measurement of the detector of the present invention.

(vi) Description of FIG. 6

As seen in FIG. 6, for current measurement, the output 600 from the detectors is fed to an off-set control shown in block 601. The output 602 from block 601 is fed to a TRACOR™ or other equivalent electrometer shown in block 603. The output 604 from TRACOR™ or other equivalent electrometer block 603 is fed to pen recorder 605 having a 1 mV range.

DESCRIPTION OF OPERATION OF PREFERRED EMBODIMENTS (i) Description of Operation of the Detector of FIG. 2

In use of this detector, which is a tube whose walls contain $Y_2O_3$ (e.g., 8 mol %) and $ZrO_2$ (e.g., 92 mol %), the detector is connected to the effluent flowing from a gas chromatograph column. A sample of gas, either oxygen or ethane, may be injected onto the chromatographic column. The gases eluted from the column produced a sharp peak. In the "simplest form" this peak was a voltage signal and in the "more sophisticated form" the peak was a current signal. In the latter case, the signal was proportional to the concentration of gas injected, except at very high concentrations. The signal for ethane is $10^5$ times greater than the signal obtained from a flame ionization detector, which is the most sensitive detector available for ethane at present. The signal for oxygen was comparable in magnitude but opposite in sign to the signal for ethane. The flame ionization detector has no response to oxygen.

The detector was fabricated as follows:

A 11 cm long 9.5 mm diameter zirconia tube was produced by slip-casting 8 mol % yttria-stabilized zirconia powder (TZ-8Y) manufactured by Tosoh Corp., and sintering at 1550° C. Pieces of platinum wire, as electrode leads, were tightly wound at the top and middle sections of the tube. Platinum ink was applied on both sides of the zirconia tube so as to form 1 cm wide bands of electrodes. The inside electrode band was electrically connected by further painting a narrow line of platinum ink to the lead wire at the top of the tube. This piece was further heat-treated at 1300° C. The lower end of the sintered tube was connected with a silicone rubber sealant to ⅛ inch copper tubing to receive the effluent gas from a gas chromatograph (GC) column via a flow diversion valve. This valve enabled the switching of the effluent flow from a flame ionization detector (FID) to the zirconia detector or vice versa. A NICHROME™ resistive heater, wound on a 14 mm quartz tube, was placed over the platinum electrode area to maintain the platinum electrode-zirconia electrolyte interface at a given elevated temperature. The temperature was monitored with a 13% rhodium platinum—platinum thermocouple placed inside the tube.

A gas chromatographic system consisting of a ⅛-inch copper tubing gas line, a ¼-inch copper tubing GC column packed with silica gel, a sample injection valve with a 0.25 ml sampling loop and zirconia and FID detectors was used for testing the detectors. To receive the effluent from the column alternatively, the detectors were connected to a two-way flow control valve with ⅛-inch copper tubing. They were so arranged as to facilitate the direct comparison of zirconia and FID detectors.

Output from the zirconia detector was processed in two ways: for voltage and current measurements. The recorder used had a 1 mV range. The voltage output from the zirconia detector was roughly 200 mV with a nitrogen carrier gas. For voltage measurements, a DC voltage divider variable from a 1:1 to a 2000:1 ratio was used. It also had the capability to take the high impedance input and to off-set the input due to the oxygen content in the carrier gas. For current measurements, a TRACOR™ electrometer was used. This arrangement enables one to make direct comparisons of sensitivities of zirconia and FID detectors. The current output from the zirconia detector, when connected to the electrometer, was in the highest attenuator range ($102 \times 10^6$) for the output from the oxygen content in the carrier gas. Therefore, an offset device consisting of an 1.5 V dry cell and a 500 ohm variable resistor was used to reduce the baseline to a lower attenuator range. The output from the voltage divider or the electrometer was fed into a FISHER™ pen recorder to be analyzed.

The zirconia detector was heated to 580° C. Ethane as a sample gas was metered with a pressure transducer and injected into the carrier gas stream. At a certain elapsed time, the sample gas emerged from the G.C. column, flowed into the zirconia detector and oxidized on the platinum electrode so as to change the electrode output. The output as a function of time was recorded on a chart paper to be analyzed manually.

It was found that the use of pure ethane caused peak saturation. Therefore, ethane was diluted with nitrogen or argon and used to examine the correlations between sample pressure and detector response. A plot was made of the detector current response against ethane pressure, where 5.17% ethane in nitrogen was used as a test gas, the detector teyperature was 583°–590° C., and the nitrogen carrier gas flow rate was 23 ml/min. A plot of the detector voltage response against ethane pressure was also made where the detector temperature was 580°–586° C. and nitrogen carrier gas flow rate was 24 ml/min. A study of these plots indicated that, as the ethane pressure increased, detector output increased gradually, and at about 0.2 torr ethane it started to increase rapidly as the oxygen partial pressure ratio approached infinity. Later it began to flatten out because of peak saturation. This behaviour can be predicted from the Nernst equation.

The electrometer output was calibrated against the amperage, and the areas of the response peak obtained were converted into the amounts of electric charge. The theoretical amounts of the electric charge required to complete the reaction of the ethane samples were also calculated and plotted against those of the electric charges from the peak areas. The slope of the plots was roughly 0.25 at lower concentrations of ethane, indicating that 25% of the sample ethane reacted at the platinum inside electrode.

Ethane was diluted to 1.040% in argon and the detector response at low sample concentrations was studied at 579°–600° C. Results show that at ethane pressures below 0.07 Torr the output of the detector correlated linearly with sample pressure. The results from the FID at similar sample pressures show that the noise level is higher from the zirconia detector, but the signal output currents from the zirconia detector are roughly $5 \times 10^5$ times higher than those from the FID detector.

(iii) Description of FIG. 3 and Its Use

In the structure of this embodiment, the carrier gas effluent from the detector top opening envelopes the outside electrode and escapes from the opening at the bottom of the dome, thus eliminating the oxygen pressure gradient between the inside and outside electrodes. When tested with argon carrier gas, it produced 130 mV output, and with the glass dome removed it produced 150 mV. With this detector, the response correlations with ethane were examined and the results show that this arrangement increased the sensitivity by about 70% over the dome-off arrangement.

The same detector was tested with a hydrogen gas sample, which is inactive to the FID detector. The plots of the results from pure hydrogen and those from 10.13% hydrogen in argon are similar to those with ethane samples.

(iv) Description of FIG. 4 and Its Use

In this embodiment, the zirconia detector tube with platinum paste electrodes was sealed in a quartz tube with two brass end pieces with rubber O-rings so that a carrier gas can separately flow through the inside and the outside of the detector tube to prevent the oxygen in the air from making contact with the detector electrodes. A carrier gas flow was split into two: one stream flows through a sample injector, a GC column and the inside channel of the detector tube, and goes out to the air through a short piece of ⅛ inch copper tubing; the other one flows through a needle valve, a flow stabilizing packed column, the channel between the quartz tube and the detector tube and goes out to the air through another short piece of ⅛ inch copper tubing. These pieces of copper tubing should, in effect, eliminate the back diffusion of air. A nichrome-wound heater with a stainless steel noise shield was placed outside the quartz tube, and a thermocouple was inserted between the heater and the quartz tube.

Using argon as a carrier gas and 0.1024% ethane in argon as a sample, the detector response was examined. The voltage response was found as a function of ethane pressure at 563° C. The current response was found as a function of ethane pressure at 564° C. Linear correlations were observed. Typical traces of response peaks at the lowest sample pressures (about $3 \times 10^{-3}$ Torr), obtained with the zirconia detector and the FID detector indicate that the FID detector produced a peak of 1 chart unit, which was almost at the detection limit, whereas the zirconia detector produced a sizable peak of 7 chart units by the current method or 19 chart units by the voltage method. The baseline of the zirconia detector tends to fluctuate slowly at random, whereas that of FID appears more stable. Except for this fluctuation, the noise level of the zirconia detector by the current method is comparable with that of the FID. The voltage method appears to be superior to the current method, but its noise level was higher so that the signal to noise ratios appeared comparable. The overall advantage of a zirconia detector over a FID detector is found to be roughly 7 fold on signal-to-noise ratio in this embodiment. While it is not desired to be limited to any particular theory, it is believed that a reduction of oxygen content in the carriers will lead to further improvements in sensitivity for the zirconia detector.

Conclusion

The zirconia detector according to this principle was found to be workable and its sensitivity appears to be superior to FID detectors.

Zirconia devices are widely used at present for detection and analysis of the oxygen content of gases and are used even in automobiles. The present invention provides oxygen sensors based on a similar principle with a rapid response time of milliseconds. The present invention has a range of degrees of specificity depending upon the sophistication of the electronics. This could range from simple detection of organic vapours for warning purposes, to a device to quantitatively measure the content of all organic vapours, to a device which will identify the class of compound contained in the organic vapours, to one which quantitatively measures the amounts of these classes, up to one which determines the elemental content of the vapours and on to a detector which indicates and identifies particular compounds and their concentrations in the gas. The present invention is inexpensive. The electronics will cost an amount in the case of a simple detection system and larger amounts depending on the degree of sophistication required in the interpretation of the data.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A method for measuring the concentration of a sample gas in an oxygen-containing carrier gas comprising the steps of:

(a) continuously flowing said oxygen-containing carrier gas which also contains said sample gas whose concentration is to be measured, by way of entry through a first inlet tube into and through a central, solid electrolyte inner detector tube, said first inlet tube being disposed at one end of said central, solid electrolyte inner detector tube, and by way of discharge through a first outlet tube therefrom at the other end thereof, said first outlet tube substantially eliminating back-diffusion of air into said central, solid electrolyte inner detector tube, said central, solid electrolyte inner detector tube comprising an oxide of a tetravalent metal doped with an oxide of an element having a valence less than four, said central solid electrolyte inner detector tube being provided with an internal electrode in contact with the interior of said central, solid electrolyte inner detector tube, said internal electrode being provided with a first, electrically-conductive output lead, and also with an external electrode which is in contact with the exterior of said central, solid electrolyte inner detector tube, said external electrode being provided with a second, electrically-conductive output lead, whereby to bathe a first interface comprising said internal electrode and the interior of said central, solid electrolyte inner detector tube only with said continuously flowing oxygen-containing carrier gas which also contains said sample gas, said interface being maintained at a predetermined temperature;

(b) continuously flowing a reference gas by way of entry through a second inlet tube into and through an annulus between said central, solid electrolyte inner detector tube and an outer, concentric non-porous tube, said second inlet tube being disposed at one end of said annulus between said central, solid electrolyte inner detector tube and said outer concentric, non-porous tube, and by way of discharge through a second outlet tube from said annulus between said central, solid electrolyte inner detector tube and said outer, concentric non-porous tube at the other end thereof, said second outlet tube substantially eliminating back-diffusion of air into said annulus, whereby to bathe a second interface comprising said external electrode and the exterior of said central, solid electrolyte inner detector tube only with said continuously flowing reference gas, said interface being maintained at the same said predetermined temperature as recited hereinabove in step (a);

(c) sealing said first inlet tube to, said first outlet tube from said second inlet tube to and said second outlet tube from said central, solid electrolyte inner detector tube and said outer concentric non-porous tube to provide a sealed unit;

(d) both said oxygen-containing carrier gas which also contains said sample gas, and said reference gas having a low level, impurity concentration of oxygen;

(e) generating an electrical signal between said electrodes, said electrical signal being directly proportional to the concentration of said sample gas to be determined; and (f) measuring said electrical signal to determine the concentration of the sample gas as a linear correlation of said electrical signal.

2. The method of claim 1 wherein said oxygen-containing carrier gas also contains an organic vapor.

3. The method of claim 2 wherein said carrier gas contains non-uniform slugs or peaks of said organic vapors.

4. The method of claim 1 wherein said electric signal which is directly measured is voltage.

5. The method of claim 1 wherein said electric signal which is directly measured is current.

6. The method of claim 1 wherein oxygen is pumped from said oxygen-containing carrier gas electrochemically through said central, solid electrolyte inner detector tube by placing a positive voltage on said external electrode which is in contact with said oxygen-containing reference gas; and by placing a negative voltage on said internal electrode which is in contact with said oxygen-containing carrier gas, which also contains organic vapor; and wherein said electrical signal generated is a current.

7. The method of claim 1 wherein the electrolyte of said central, solid electrolyte inner detector tube comprises an oxide selected from the group consisting of zirconia, thoria and hafnia.

8. The method of claim 7 wherein said oxide of said central, solid electrolyte inner detector tube is doped with an oxide selected from the group consisting of yttria, lime and magnesia.

9. The method of claim 8 wherein said solid electrolyte inner detector tube is 92 mol % zirconia/8 mol % yttria.

10. The method of claim 1 wherein said internal electrode is in the form of a band formed of platinum.

11. The method of claim 1 wherein said external electrode is in the form of at least one strip of platinum along the longitudinal axis of said central, solid electrolyte inner detector tube.

12. The method of claim 1 wherein said external electrode is in the form of an encircling band of platinum around said central solid electrolyte inner detector tube.

13. The method of claim 1 wherein said outer, concentric, non-porous tube is formed of quartz.

14. The method of claim 1 wherein the electrolyte of said central, solid electrolyte inner detector tube is 92 mol % zirconia/8 mol % yttria; wherein said internal electrode is in the form of a band formed of platinum; wherein said external electrode is in the form of at least one strip of platinum along the longitudinal axis of said solid electrolyte tube; and wherein said outer, concentric, non-porous tube is formed of quartz.

15. The method of claim 1 wherein said central, solid electrolyte inner detector tube is 92 mol % zirconia/8 mol % yttria; wherein said internal electrode is in the form of a band formed of platinum; wherein said external electrode is in the form of a band of platinum; and wherein said outer, concentric non-porous tube is formed of quartz.

16. The method of claim 1 wherein said internal electrode is in the form of a platinum band at the mid-region of said central solid electrolyte inner detector tube; and wherein said external electrode is in the form of a platinum band at the mid-region of said central solid electrolyte inner detector tube.

17. The method of claim 1 wherein said predetermined temperature is maintained at about 540° to 695° C.

18. The method of claim 17 including the step of monitoring said predetermined temperature.

19. The method of claim 18 wherein said step of monitoring said temperature is carried out using a rhodium/platinum-platinum thermocouple.

* * * * *